United States Patent [19]
Klein et al.

[11] Patent Number: 5,430,167
[45] Date of Patent: Jul. 4, 1995

[54] SILANES WITH HYDROPHILIC GROUPS, THEIR SYNTHESIS AND USE AS SURFACTANTS IN AQUEOUS MEDIA

[75] Inventors: Klaus-Dieter Klein, Mülheim; Wilfried Knott; Götz Koerner, both of Essen, all of Germany

[73] Assignee: Th. Goldschmidt AG, Essen, Germany

[21] Appl. No.: 265,075

[22] Filed: Jun. 24, 1994

[30] Foreign Application Priority Data

Jun. 24, 1993 [DE] Germany .................. 43 20 920.3

[51] Int. Cl.$^6$ .................. C07F 7/08; C07F 7/18
[52] U.S. Cl. .................. 556/445; 556/449; 252/351; 252/353
[58] Field of Search ........... 556/449, 445; 252/351, 252/353

[56] References Cited

U.S. PATENT DOCUMENTS

| | | | |
|---|---|---|---|
| 2,629,727 | 2/1953 | Speier | 556/449 |
| 2,924,588 | 2/1960 | Speier | 556/449 |
| 2,983,745 | 5/1961 | Speier | 556/449 |
| 3,159,496 | 12/1964 | Rossmy | 556/449 |
| 5,113,005 | 5/1992 | Celebuski | 556/449 |
| 5,159,095 | 10/1992 | Celebuski | 556/449 |

FOREIGN PATENT DOCUMENTS

| | | |
|---|---|---|
| 0367381 | 5/1990 | European Pat. Off. . |
| 4141046 | 2/1993 | Germany . |
| 1520421 | 8/1978 | United Kingdom . |

OTHER PUBLICATIONS

Die temperaturabhängigkeit der Benetzung, Aug. 12, 1969, 5 pages, by A. W. Neumann.
Syntheses and Properties of Surfactants . . . , 1970, 7 pages, Hirohisa Maki, et al.
Syntheses and Properties of Surfactants . . . , 1970, 5 pages, Hirohisa Maki, et al.

*Primary Examiner*—Paul F. Shaver
*Attorney, Agent, or Firm*—Anderson Kill & Oshinsky Olick

[57] ABSTRACT

Silanes of the general formula

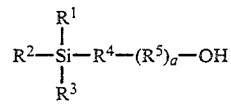

wherein
$R^1$, $R^2$ and $R^3$ in the molecule are the same or different and represent aliphatic hydrocarbon groups,
$R^4$ is a divalent hydrocarbon group with 3 to 14 carbon atoms,
$R^5$ is a group having the formula $-O(CH_2)_b-$ or a polyether group having the formula $-(OC_nH_{2n})_c-$, wherein
  b has a value of 1 to 6,
  n has an average value of 2 to 2.5
  c has a value of 1 to 10, and
a is 0 or 1, which fulfill the condition that they lower the surface tension of a 1% by weight aqueous solution to a value of $\leq 25$ mN/m at 25° C., measured with a Du Noöy tensiometer. The silanes are biologically degradable, resistant to hydrolysis and have pronounced surface active properties.

15 Claims, No Drawings

SILANES WITH HYDROPHILIC GROUPS, THEIR SYNTHESIS AND USE AS SURFACTANTS IN AQUEOUS MEDIA

FIELD OF THE INVENTION

The invention relates to novel silanes with hydrophilic groups, their synthesis and their use as surfactants in aqueous media. More particularly, it relates to hydrolysis-resistant silane surfactants, which have the ability to drastically lower the surface tension of aqueous media. The concept of "aqueous" media is understood to include also those media, which consist predominantly of water and additionally may contain water-soluble or water-miscible organic solvents.

BACKGROUND INFORMATION

It is known from the state of the art that organomodified siloxanes, such as polyether siloxanes or polysiloxanes, having substituents with anionic, cationic or amphoteric groups, an appropriately selected structure and a balanced ratio of hydrophilic to hydrophobic groups, can lower the surface tension of aqueous solutions to a pronounced degree.

Surfactants with at least three silicon atoms are described in the German patent 41 41 046. They correspond to the general formula

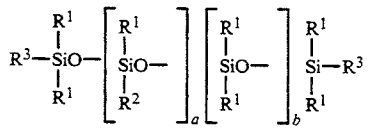

wherein $R^1$ are methyl or phenyl groups, with the proviso that at least 90% of the $R^1$ groups are methyl groups, $R^2$ is identical with $R^1$ or $-(CH_2)_6-SO_3^-.M^+$, wherein $M^+$ is an alkali, $\frac{1}{2}$ an alkali earth or optionally an alkyl-substituted ammonium ion, $R^3$ is identical with $R^1$ or $R^2$, with the proviso that at least one $R^2$ or $R^3$ group in an average molecule is a $-(CH_2)_6-OSO_3^-.M^+$ group, a has a numerical value of 0 to 5, and b has a numerical value of 0 to 5.

In neutral, aqueous media, the selected trisiloxanehexyl sulfates having three silicon atoms greatly decrease the surface tension of neutral media to values of about 21 mN/m. However, in acidic or alkaline solutions, they are not stable and, due to hydrolysis of the Si—O—Si bonds and renewed condensation of the hydrolysis products to higher molecular weight oligomers, very rapidly lose their effectiveness and partly become insoluble in aqueous media.

Surfactants with a low content of silicon atoms are furthermore described in the European publication 0 367 381 (A2) and in the British patent 1,520,421.

The European publication 0 367 381 (A2) relates to organosilicon compounds of the general formula

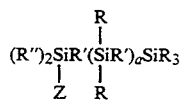

wherein R independently of one another represent an alkyl, aryl, halogenated alkyl or halogenated aryl group with up to 18 carbon atoms, each R' represents an alkylene group, which separates adjacent silicon atoms from one another by up to 6 carbon atoms and R" independently of one another represent R or, when a is equal to zero, the $R_3SiR'$ group. Z is a hydrophilic substituent, which contains sulfur, nitrogen or phosphorus, a carboxy-functional group or its salt. a has a value of 0, 1 or 2.

It follows from this that the organosilicon group, by definition, contains at least two silicon atoms. The synthesis of these carbosilanes is relatively expensive and is accomplished, for example, by a method similar to a Grignard reaction. After that, carbosilane surfactants, with a quaternary, sulfonate or betaine structure, are synthesized by means of a hydrosilylation of, for example, allyl glycidyl ether or allylamine and well-known subsequent reactions. The substances, so obtained, lower the surface tension of a 1% solution in distilled water to 23 to 25 mN/m.

In the British patent 1,520,421, carbosilane surfactants and their synthesis are described. They have the general formula

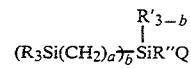

wherein

R is a methyl, ethyl, propyl or trifluoropropyl group, with the proviso that at least 50% of the R groups are methyl groups, R' is an alkyl group with 1 to 6 carbon atoms, R" is a divalent aliphatic hydrocarbon group with 2 to 6 carbon atoms, which connects Q and the adjacent silicon atom by means of a bridge of at least 2 carbon atoms, Q is the $-O(C_2H_4O)_cX$ group, wherein c has a value of 3 to 12 and X is a hydrogen group, R''' is

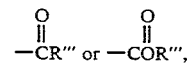

in which R''' is an alkyl group with 1 to 5 carbon atoms, and a=1 or 2 and b=2 or 3.

According to definition, at least two silicon atoms must be present here also. In application tests, these compounds exhibit remarkable foaming properties.

It was known to those skilled in the art that the surfactant properties of the compounds within groups of known carbosilanes with comparable structure deteriorate as the number of silicon atoms is decreased, in particular, as the number of silicon atoms is decreased from 4 to 3 or 2. This observation is embodied in the theory of Neumann (A. W. Neumann, D. Renzow, Zeitschrift f. Phys. Chem., new issue 68, 11 (1969)), which states that the permethylated surface of the siloxane backbone is responsible for the lowering of the surface tensions of aqueous solutions to values below 30 to 40 mN/m.

Furthermore, reference is made to the Japanese publications of H. Maki et al. in YUKAGAGU 19, No. 4, page 51 ff. and YUKAGAGU 19, No. 11, page 23 ff., both from 1970, wherein defined compounds of the formula

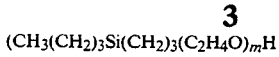

are described, in which n=4.2 or 7.0 and m=10 or 17. However, these compounds lower the surface tension of a 1% by weight solution only to values not less than 26.5 mN/m.

In these Japanese publications, quaternary nitrogen compounds of the formula

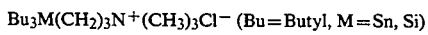

are also described. Admittedly, these compounds have bacteriostatic activity; however, they are not very surface active. The best representatives of these quaternary compounds bring about a surface tension lowering to 32 mN/m in a 1% aqueous solution.

The present invention is based on the surprising finding that, in contrast to general theoretical knowledge, as expressed, for example, in the theory of Neumann, selected silanes, that is, compounds with only a single silicon atom, for which, however, the ratio of hydrophilic to hydrophobic parts of the molecule is balanced, lower the surface tension of water extraordinarily effectively and, in contrast to the siloxane surfactants, are resistant to hydrolysis for days and weeks, even in acidic and alkaline media. A further and unforeseeable advantage of the inventive silanes is their complete biological degradability, which makes them particularly suitable for use as surfactants. Such a profile of properties could not be inferred from the state of the art and contradicts previously customary assumptions concerning the structural requirements, which organosilicon compounds should meet in order to exhibit surface tension-lowering properties in aqueous systems.

OBJECT OF THE INVENTION

An object of the present invention are inventive silanes. Another object of the invention is the synthesis of the inventive silanes. Yet another object of the invention is a method of reducing surface tension of aqueous media by adding the inventive silanes. A further object of the invention is an aqueous solution containing 1% by weight of silanes whereby the surface tension of the solution is reduced.

The inventive silanes of the general formula

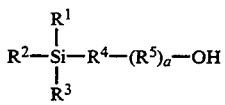

wherein
R$^1$, R$^2$ and R$^3$ in the molecule are the same or different and represent aliphatic hydrocarbon groups,
R$^4$ is a divalent hydrocarbon group with 3 to 14 carbon atoms,
R$^5$ is a group having the formula —O(CH$_2$)$_b$— or a polyether group having the formula —(OC$_n$H$_{2n}$)$_c$—, wherein
b has a value of 1 to 6,
n has an average value of 2 to 2.5,
c has a value of 1 to 10, and
a is 0 or 1,
which fulfill the condition that they lower the surface tension of a 1% by weight aqueous solution to a value of ≦25 mN/m at 25° C., measured with a Du Noüy tensionmeter.

SUMMARY OF THE INVENTION

Examples of preferred R$^1$, R$^2$ and R$^3$ groups are methyl, ethyl, propyl or butyl groups.

Preferably, at least 90% of the R$^1$, R$^2$ and R$^3$ groups are methyl groups.

R$^4$ is a divalent hydrocarbon group with 3 to 14 carbon atoms, such as —C$_3$H$_6$—, —C$_5$H$_{10}$—, C$_6$H$_{12}$— or C$_{11}$H$_{22}$— groups. The R$^4$ groups can be substituted, for example, by lateral alkyl groups or halogen groups. However, linear hydrocarbon groups are preferred.

Further examples of R$^4$ groups are groups of the formula

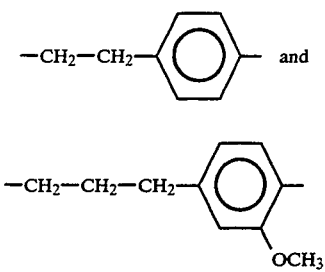

Preferably, R$^4$ is a divalent, aliphatic hydrocarbon group with 3 to 9 carbon atoms, particularly with 3 to 6 carbon atoms.

R$^5$ is a group having the formula —O(CH$_2$)$_b$— or a polyether group having the formula —(OC$_n$H$_{2n}$)$_c$—, wherein b has a value of 1 to 6, n has an average value of 2 to 2.5 and c has a value of 1 to 10. Examples of such groups are the —OCH$_2$—, —(CH$_2$)$_4$—, —(CH$_2$)$_6$—, —(OC$_2$H$_4$)$_8$— and —(OCH(CH$_3$)CH$_5$)$_5$— groups.

n preferably has a value of 2.0, so that, in this case, all oxyalkylene units are oxyethylene units. The subscript c indicates the number of these units and has a value of 1 to 10 and preferably of 3 to 6. a has a value of 0 or 1.

Examples of the inventive silanes are (CH$_3$)$_3$Si(CH$_2$)$_3$—OCH$_2$CH$_2$—OH;
(CH$_3$)$_3$Si(CH$_2$)$_6$—O—(CH$_2$CH$_2$O—)$_4$H;
(CH$_3$)$_3$Si(CH$_2$)$_6$—O—(CH$_2$CH$_2$O—)$_2$H;
(CH$_3$)$_3$Si(CH$_2$)hd—O—(CH$_2$CH$_2$O—)$_6$H.

A further object of the invention is the synthesis of the inventive compounds. The compounds can be synthesized by an addition reaction between silanes of the general formula

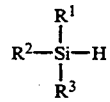

in each case in the presence of known hydrosilylation catalyst and
a) compounds of the general formula

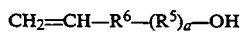

wherein R$^6$ is a divalent, aliphatic hydrocarbon group with 1 to 12 carbon atoms, or
b) compounds of the general formula

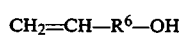

and, in the event of variation b) of the method, c moles of alkylene oxides of the general formula

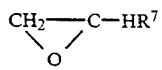

wherein $R^7$ is a hydrogen group or an alkyl group with 1 or 2 carbon atoms and the alkylene oxides have, on the average, 2 to 2.5 carbon atoms,
are added to the terminal hydroxyl group in the presence of an alkaline catalyst or a Lewis acid.

$R^6$ preferably is a divalent hydrocarbon groups with 1 to 7 and particularly 1 to 4 carbon atoms.

Especially ethylene oxide and propylene oxide are used as alkylene oxides. An equimolar mixture of the two alkylene oxides thus leads to products, in which n has a value of 2.5. The possibility also exists of also using smaller amounts of butylene oxide; however the condition must be fulfilled that n may not exceed 2.5.

The known catalysts are suitable for the addition reaction between alkylene oxides and the terminal OH group of the silanes. As alkaline catalysts, sodium hydroxide or potassium hydroxide or their alcoholates, particularly sodium or potassium methylate can be used. As Lewis acid, $BF_3$ etherate is particularly preferred. If different alkylene oxides are added, the corresponding alkylene oxide mixtures can be used and products are obtained with a random distribution of the alkylene oxide units. The different alkylene oxide units can also be added on consecutively, a blockwise arrangement of the alkylene oxide units being obtained. The addition reaction of the alkylene units preferably is carried out at an elevated pressure in a closed vessel.

For optimizing the interfacial properties of the inventive compounds, the hydrophilic and hydrophobic parts of their molecules must be present in a balanced ratio. The hydrophobic properties can be affected by the $R^1$, $R^2$, $R^3$ and $R^4$ groups. The higher the carbon content of these groups, the more hydrophobic is the inventive silane. The hydrophilicity is determined by the $(R^5)_a$ group and, in particular, by the value of the subscripts n and c. Within the given range of numerical values, the lower the numerical value of n and the higher the numerical value of c, the more hydrophilic is the silane surfactant. This effect on the surfactant properties is explained in greater detail in the Examples and thus becomes easily understandable to those skilled in the art. Only a few reasonable preliminary experiments, which do not involve any inventive effort, are required for achieving the desired properties, especially for achieving the desired lowering in surface tension.

Preferably, the hydrosilylation is carried out at an elevated temperature of up to 130° C. and in the presence of a catalyst. Platinum catalysts, in particular, are suitable catalysts. Such hydrosilylation reactions are familiar to those skilled in the art.

A further object of the invention is the use of the inventive silanes as surfactants in aqueous media. In this connection, it is possible to reduce the surface tension of aqueous solutions to values of about 22 mN/m by the addition of 1% by weight of the inventive compounds. Moreover, the biological degradability of the inventive compounds is of quite special importance. It is supplemented by the resistance of the silane surfactants to hydrolysis.

Important, possible uses for the inventive silane surfactants are, for example:

as wetting agents:
in preparations for the treatment of plants (agricultural formulations); to improve the wetting of substrates with a low surface free energy, such as polyethylene or polypropylene surfaces; for use in the paint industry; for the production of photographic films; in electroplating;

as dispersant:
for dispersions paints, pigments and fillers;

as emulsifiers or additives in the textile industry for the preparation of textile auxiliaries, softeners, lubricants, antistatic preparations; as dyeing aids;

as surfactants in general:
for use in fire extinguishers; as foam stabilizers, as surface active additives for high-speed printing inks, adhesives, dispersion adhesives, melt adhesives, use in detergents; as additives for industrial cleaners;

as raw material for use in cosmetics, shampoos, shower gels.

in technical applications and in the house:
as anti-fogging aid; for use in dish-washing detergents, detergents, toilet cleaners, automatic gloss emulsions.

The synthesis of the inventive compounds and their properties are described in even greater detail in the following Examples, it being understood that the Examples are being provided by way of illustration and not by way of limitation.

EXAMPLE 1 a) Synthesis of (6-Hydroxyhexyl)trimethylsilane (Intermediate, Not of the Invention)

1-Hexene-5-ol (28.7 g, 0.287 moles) and 3 mg of platinum catalyst are weighed into a 300 mL laboratory autoclave. Under an argon blanket, the autoclave with contents is now cooled in an acetone/dry ice bath and 22.4 g of trimethylsilane (0.299 moles with a boiling point of 6.7° C.) are siphoned over from the condensed phase. The autoclave is closed and heated to 130° C. At the same time, the internal pressure increases to 13.7 bar, only to drop once again then to about 5.7 bar. This drop in pressure indicates a reaction.

After the pressure in the autoclave has been relieved, which is done after the autoclave has been cooled to room temperature, the contents are freed from the platinum catalyst by filtration (weight: 50.7 g, mass loss: 0.9 g). Hydroxyl number—theoretical: 321.7; actual: 306.0

$^{29}Si$-NMR and $^1H$-NMR spectroscopic analysis reveal the structure of the product to be as follows:

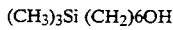

The product is freed from highly volatile components at 20° C. under the vacuum of an oil pump.

b) Synthesis of a (Polyoxyethylene)Trimethylsilane by the Ethoxylation of (Hydroxyhexyl) Trimethylsilane (of the Invention)

Hydroxyhexyltrimethylsilane (20.0 g, 0.11 moles) and 0.82 g of a 50% boron trifluoride solution in ether are added to a 3-neck flask, which is equipped with an intensive condenser, thermometer, dropping funnel equipped with cooling mantle and a nitrogen connection. Condensed ethylene oxide (21.1 g, 0.48 moles) is then slowly added dropwise. The exothermic reaction is counteracted with an ice bath so that the internal temperature does not exceed 20° to 30° C. After that, stirring is continued for two hours at room temperature. After neutralization with 1.50 g of sodium hydrogen carbonate and 0.41 g of water (1% by weight), the volatile components are removed from the product at 90° C. under the vacuum of a water jet pump.

The subsequent filtration with prior addition of filter aids results in a weakly yellow, clear product which, according to $^1$H spectroscopy as well as gel permeation chromatography, has 4.2 oxyalkylene units and accordingly can be reproduced by the following average formula:

$(CH_3)_3Si-(CH_2)_6-O-(CH_2CH_2O)_{4.2}-H$

This product is made up as a 1% by weight or a 0.1% by weight solution, the spreadability of which (50 μL droplet) is investigated after 24 hours on a polypropylene sheet.

TABLE 1

| Concentration (% by weight) | Spreading (mm) on Polypropylene Sheet |
| --- | --- |
| 1.0 | 65 |
| 0.1 | 75 |

Starting out from (hydroxyhexyl)trimethylsilane, (hydroxypropyl)trimethylsilane and (hydroxyundecyl)trimethylsilane, inventive compounds are synthesized by the above method by varying the number and type of oxyalkylene unit and the properties of these compounds are shown in the following Tables.

TABLE 2

| | Alkoxylation Products of (Hydroxyhexyl)trimethylsilane | |
| --- | --- | --- |
| EO/PO | Spreading (mm) (0.1% by weight) | Surface Tension (mN/m) (0.1% by weight Solution) |
| 1.5/0 | 80 | 23.1 |
| 2.8/0 | 80 | 22.4 |
| 4.0/0 | 75 | 23.0 |
| 4.7/0 | 75 | 22.7 |
| 8.3/0 | 20 | 25.2 |
| 0 /5.0 | insoluble | n.d. |
| 4.0/1.0 (random) | 55 | 23.8 |
| 4.0/1.0 (first EO; then PO) | 20 (cloudy solution) | 24.9 |

"Random" in the above Table means that ethylene oxide and propylene oxide are added in the form of a mixture, so that a random distribution of the alkylene oxides takes place.

The expression "first EO; then PO" means that the given amount of ethylene oxide is added first and the given amount of propylene oxide is added subsequently, so that a blockwise distribution of oxyalkylene units results.

The abbreviation "n.d." means that the value cannot be determined.

TABLE 3

| | Alkoxylation Products of (Hydroxypropyl)trimethylsilane | |
| --- | --- | --- |
| EO/PO | Spreading (mm) (1% by weight) | Surface Tension (mN/m) (1% by weight Solution) |
| 2.4/0 | 60 | 23.1 |
| 4.3/0 | 75 | 23.1 |
| 8.3/0 | 20 | 24.1 |
| 10.5/0 | 15 | 25.3 |
| 0 /5 | insoluble | n.b. |
| 5 /1 (first PO; then EO) | 60 | 23.9 |
| 5 /2 (first PO; then EO) | 30 | 24.9 |
| 5 /1 (random) | 60 | 23.2 |

TABLE 4

| | Alkoxylation Products of (Hydroxyundecyl)trimethylsilane | |
| --- | --- | --- |
| EO/PO | Spreading (mm) (1% by weight) | Surface Tension (mN/m) (1% by weight Solution) |
| 5/0 | 40 | 23.9 |

EXAMPLE 2

Synthesis of a Polyoxyalkylenetrimethylsilane Having the Formula $(CH_3)_3Si(CH_2)_6(OCH_2CH_2)_4OH$ by Hydrosilylation (of the Invention)

To a 300 mL laboratory autoclave are added 88.14 g of hexenyl polyether having the formula $CH_2=CH(CH_2)_4(OCH_2CH_2)_4OH$ (0.3 moles with an hydroxyl number of 203.4 and an iodine number of 86.4) and 5 mg of platinum catalyst. The autoclave and the contents, in a protective atmosphere of argon, are cooled in an acetone/dry ice bath and 23.34 g of trimethylsilane (0.315 moles) are siphoned over. The autoclave is closed and heated to 130° C. At the same time, the internal pressure increases to 8.0 bar, only to drop then once again to about 3.5 bar.

After the autoclave is cooled to room temperature and the pressure is relieved, the contents, weighing 109.0 g and thus indicating a mass loss of 0.6 g, are freed from the platinum catalyst by filtration.

TABLE 5

| Decrease in the Surface Tension as a Function of the Concentration of an Aqueous Solution | |
| --- | --- |
| Concentration (% by weight) | Surface Tension (mN/m) at 25° C. |
| 1.0 | 23.0 |
| 0.4 | 23.0 |
| 0.3 | 23.1 |
| 0.15 | 23.8 |
| 0.09 | 30.7 |
| 0.07 | 34.7 |

TABLE 6

| Spreading Capability as a Function of the Concentration of an Aqueous Solution | |
| --- | --- |
| Concentration (% by weight) | Spreading (mm) |
| 0.01 | 8 |
| 0.1 | 85 |
| 0.3 | 73 |
| 0.5 | 61 |
| 1.0 | 48 |

There is seen to be a concentration dependent maximum at a concentration of 0.1% by weight.

EXAMPLE 3

Synthesis of Further Inventive Compounds and Their Properties

The following compounds are synthesized as described in the preceding examples:

TMS-PE 1 = TMS—C$_3$—O—CH$_2$CH$_2$OH
TMS-PE 2 = TMS—C$_6$—O—(CH$_2$CH$_2$O)$_2$H
TMS-PE 3 = TMS—C$_6$—O—(CH$_2$CH$_2$O)$_4$H
TMS-PE 4 = TMS—C$_6$—O—(CH$_2$CH$_2$O)$_6$H

TMS = Trimethylsilyl group

To begin with, aqueous solutions with a concentration of 1% by weight of product are prepared and their surface tension is determined by the Du Noüy method.

In order to determine the wetting capability, the spreading of a 50 μL droplet of the 1% surfactant solution is measured on a polypropylene sheet over the maximum extent of the area. Under these conditions, pure water gives a blank value of 8 mm. The long-term resistance to hydrolysis is also followed by observing the wetting property of a 1% solution.

TABLE 7

| Product | Solution | Surface Tension (mN/m) | Spreading (mm) on Polypropylene Sheet |
|---------|----------|------------------------|---------------------------------------|
| TMS-PE 1 | cloudy | 23.7 | 28 |
| TMS-PE 2 | cloudy | 23.2 | 70 |
| TMS-PE 3 | cloudy | 23.0 | 48 |
| TMS-PE 4 | clear  | 24.1 | 35 |

EXAMPLE 4

The Biological Degradability of the Inventive Compounds

The biological degradability of the product from Example 1 b) is tested by a method based on the OECD guidelines (OECD 301 D).

Under conditions of the test method, it amounts to 88% BOD (BOD=biological oxygen demand) of the COD (COD=chemical oxygen demand) after 28 days. The validity of this result follows freely from the fact that the control substance, sodium acetate, is degraded by more than 60% in the same period.

We claim:

1. Silanes of the general formula

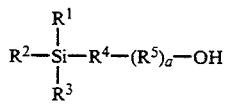

wherein
$R^1$, $R^2$ and $R^3$ in a molecule are the same or different and represent aliphatic hydrocarbon groups,
$R^4$ is a divalent hydrocarbon group with 3 to 14 carbon atoms,
$R^5$ is a group having the formula $-O(CH_2)_b-$ or a polyether group having the formula $-(OC_nH_{2n})_c-$, wherein
b has a value of 1 to 6,
n has an average value of 2 to 2.5,
c has a value of 1 to 10, and
is 1,
said silanes having further the property of lowering the surface tension of a 1% by weight aqueous solution to a value of $\leq 25$ mN/m at 25° C.

2. The silanes of claim 1, further comprising that $R^1$, $R^2$ and $R^3$ are alkyl groups with 1 to 4 carbon atoms.

3. The silanes of claim 2, further comprising that at least 90% of the $R^1$, $R^2$ and $R^3$ groups are methyl.

4. The silanes of claims 1 or 2, further comprising that the $R^4$ group is a divalent aliphatic hydrocarbon group with 3 to 14 carbon atoms.

5. The silanes of claim 4, further comprising that the $R^4$ group is a divalent aliphatic hydrocarbon group with 3 to 9 carbon atoms.

6. The silanes of claim 5, further comprising that the $R^4$ group is a divalent aliphatic hydrocarbon group with 3 to 6 carbon atoms.

7. The silanes of claims 1 or 2, further comprising that $R^5$ is a polyether group, in which n has a value of 2 and c has a value of 3 to 6.

8. A method for the synthesis of silanes of the general formula

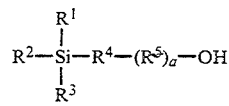

wherein
$R^1$, $R^2$ and $R^3$ in a molecule are the same or different and represent aliphatic hydrocarbon groups,
$R^4$ is a divalent hydrocarbon group with 3 to 14 carbon atoms,
$R^5$ is a group having the formula $-O(CH_2)_b-$ or a polyether group having the formula $-(OC_nH_{2n})_c-$, wherein
b has a value of 1 to 6,
n has an average value of 2 to 2.5,
c has a value of 1 to 10, and
a is 0 or 1,
said silanes having further the property of lowering the surface tension of a 1% by weight aqueous solution to a value of $\leq 25$ mN/m at 25° C., comprising the steps of adding silanes of the general formula

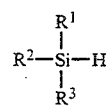

in presence of a hydrosilylation catalyst to
a) compounds of the general formula

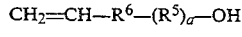

wherein $R^6$ is a divalent, aliphatic hydrocarbon group with 1 to 4 carbon atoms, or
b) compounds of the general formula

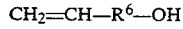

in an addition reaction and, adding in the case of compound b) above, c molecules of alkylene oxides of the general formula

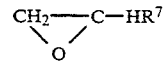

wherein $R^7$ is a hydrogen group or an alkyl group with 1 or 2 carbon atoms and the alkylene oxides have, on average, 2 to 2.5 carbon atoms,
in presence of an alkaline catalyst or a Lewis acid.

9. The method of claim 8, further comprising that the hydrosilylation is carried out at an elevated temperature, or in presence of a solvent or both.

10. The method of claims 8 or 9, further comprising that the hydrosilylation is carried out in presence of a platinum catalyst.

11. The method of claim 8, further comprising that $R^1$, $R^2$ and $R^3$ are alkyl groups with 1 to 4 carbon atoms.

12. The method of claim 8, further comprising that at least 90% of $R^1$, $R^2$ and $R^3$ groups are methyl.

13. The method of claim 8, further comprising that $R^5$ is a polyether group, in which n has a value of 2 and c has a value of 3 to 6.

14. A method of reducing the surface tension of aqueous media comprising adding to the media an effective amount of silanes of the general formula

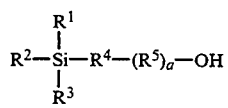

wherein $R^1$, $R^2$ and $R^3$ in a molecule are the same or different and represent aliphatic hydrocarbon groups, $R^4$ is a divalent hydrocarbon group with 3 to 14 carbon atoms, $R^5$ is a group having the formula $-O(CH_2)_b-$ or a polyether group having the formula $-(OC_nH_{2n})_c-$, wherein b has a value of 1 to 6, n has an average value of 2 to 2.5, c has a value of 1 to 10, and a is 0 or 1, said silanes having further the property of lowering the surface tension of a 1% by weight aqueous solution to a value of $\leq 25$ mN/m at 25° C., as a hydrolysis-resistant biologically degradable surfactant.

15. An aqueous solution containing 1% by weight of silanes of claims 1 or 2, whereby the surface tension of the solution is reduced.

* * * * *

UNITED STATES PATENT AND TRADEMARK OFFICE
CERTIFICATE OF CORRECTION

PATENT NO. : 5,430,167
DATED : July 4, 1995
INVENTOR(S) : Klein, et al

It is certified that error appears in the above-identified patent and that said Letters Patent is hereby corrected as shown below:

In column 9, line 17, from the bottom, it should read:

--a-- is 1.

Signed and Sealed this

Sixth Day of January, 1998

Attest:

BRUCE LEHMAN

Attesting Officer

Commissioner of Patents and Trademarks